(12) United States Patent
Verduijn et al.

(10) Patent No.: US 6,977,320 B2
(45) Date of Patent: *Dec. 20, 2005

(54) ZEOLITE CATALYST AND USE FOR HYDROCARBON CONVERSION

(75) Inventors: Johannes Petrus Verduijn, deceased, late of Leefdaal (BE); by Jannetje Maatje van den Berge, legal representative, Oostvoorne (NL); Gary D. Mohr, League City, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/126,597

(22) Filed: Apr. 19, 2002

(65) Prior Publication Data

US 2002/0187891 A1 Dec. 12, 2002

Related U.S. Application Data

(63) Continuation of application No. 08/865,343, filed on May 29, 1997, now abandoned.
(60) Provisional application No. 60/018,547, filed on May 29, 1996.

(51) Int. Cl.$^7$ ................................................ C07C 5/22
(52) U.S. Cl. ........................................................ 585/475
(58) Field of Search ................................ 585/475; 502/67

(56) References Cited

U.S. PATENT DOCUMENTS

| 4,091,007 A | 5/1978 | Dwyer et al. ............ 260/448 C |
| 4,289,607 A | 9/1981 | Kokotailo .................... 208/120 |
| 4,358,362 A | 11/1982 | Smith et al. .................... 208/91 |
| 4,358,395 A | 11/1982 | Haag et al. .............. 252/411 R |
| 4,381,255 A | 4/1983 | Nozemack et al. ...... 252/455 Z |
| 4,381,256 A | 4/1983 | Hildebrandt ............ 252/455 Z |
| 4,522,705 A | 6/1985 | Chu et al. .................... 208/120 |
| 4,533,649 A | 8/1985 | Ball et al. ...................... 502/71 |
| 4,847,224 A | 7/1989 | Fajula et al. ................... 502/67 |
| 4,872,968 A | 10/1989 | Bowes ......................... 208/111 |
| 4,977,120 A | 12/1990 | Sakurada et al. .............. 502/64 |
| 5,053,374 A | 10/1991 | Absil et al. .................... 502/64 |
| 5,098,894 A | 3/1992 | Sakurada et al. ............. 502/66 |
| 5,145,659 A | 9/1992 | McWilliams ................. 423/328 |
| 5,157,198 A | 10/1992 | Raatz et al. ................. 585/739 |
| 5,182,242 A | 1/1993 | Marler ......................... 502/66 |
| 5,248,643 A | 9/1993 | Patil et al. ..................... 502/67 |
| 5,460,796 A | 10/1995 | Verduijn ..................... 423/700 |
| 5,516,956 A | 5/1996 | Abichandani et al. ...... 585/481 |
| 5,614,454 A | 3/1997 | Galperin et al. .............. 502/66 |
| 5,665,325 A | 9/1997 | Verduijn ..................... 423/709 |
| 5,993,642 A | 11/1999 | Mohr et al. .................... 208/46 |
| 6,040,259 A | 3/2000 | Mohr et al. .................... 502/67 |
| 6,051,051 A | 4/2000 | Hees et al. ..................... 95/96 |
| 6,111,157 A | 8/2000 | Hendriksen et al. ......... 585/467 |
| 6,150,293 A | 11/2000 | Verduijn et al. .............. 502/67 |
| 6,198,013 B1 * | 3/2001 | Mohr et al. .................. 585/475 |
| 6,350,428 B1 | 2/2002 | Verduijn et al. ............. 423/702 |
| 6,458,736 B2 | 10/2002 | Mohr et al. .................... 502/67 |
| 6,504,074 B2 | 1/2003 | Verduijn et al. ............. 585/475 |
| 2002/0137977 A1 | 9/2002 | Hendriksen et al. ........ 585/471 |

FOREIGN PATENT DOCUMENTS

| CN | 11059/35 A | 8/1995 | ............ B01J/20/18 |
| DE | 4 440 231 | 7/1995 | |
| EP | 0 109 962 | 6/1984 | |
| EP | 0284206 | 9/1988 | ........... C01B/33/34 |
| WO | WO 96/16004 | 5/1996 | |

OTHER PUBLICATIONS

Structure Type Index. Internet Search Document. pp. 1–10.
Chemical Abstracts, vol. 101, No. 9, Aug. 26, 1984 Columbus, Ohio US; abstract No. 72405n, p. 614.
Chemical Abstracts, vol. 85, No. 13, Sep. 27 1976 Columbus, Ohio US; abstract No. 94018s, p. 604.

* cited by examiner

*Primary Examiner*—Thuan D. Dang (57) ABSTRACT

There is provided a zeolite bound zeolite catalyst which can be tailored to optimize its performance and a process for converting hydrocarbons utilizing the zeolite bound zeolite catalyst. The zeolite bound zeolite catalyst comprises a first zeolite and a binder comprising a second zeolite. The structure type of the second zeolite is different from the structure type of the first zeolite. The zeolite bound zeolite finds particular application in hydrocarbon conversion process, e.g., catalytic cracking, alkylation, disproportional of toluene, isomerization, and transalkylation reactions.

15 Claims, 1 Drawing Sheet

ZEOLITE CATALYST AND USE FOR HYDROCARBON CONVERSION

This application is a continuation of application Ser. No. 08/865,343, filed May 29, 1997, now abandoned, which claims the benefit of Provisional application Ser. No. 60/018,547, filed May 29, 1996.

FIELD OF THE INVENTION

This invention relates to zeolite bound zeolite catalyst which can be tailored to optimize its performance and the use of the zeolite bound zeolite catalyst for hydrocarbon conversion processes.

BACKGROUND OF THE INVENTION

Crystalline microporous molecular sieves, both natural and synthetic, have been demonstrated to have catalytic properties for various types of hydrocarbon conversion processes. In addition, the crystalline microporous molecular sieves have been used as adsorbents and catalyst carriers for various types of hydrocarbon conversion processes, and other applications. These molecular sieves are ordered, porous, crystalline material having a definite crystalline structure as determined by x-ray diffraction, within which there are a large number of smaller cavities which may be interconnected by a number of still smaller channels or pores. The dimensions of these channels or pores are such as to allow for adsorption of molecules with certain dimensions while rejecting those of large dimensions. The interstitial spaces or channels formed by the crystalline network enable molecular sieves such as crystalline silicates, aluminosilicates, crystalline silicoalumino phosphates, and crystalline aluminophosphates, to be used as molecular sieves in separation processes and catalysts and catalyst supports in a wide variety of hydrocarbon conversion processes.

Within a pore of the crystalline molecular sieve, hydrocarbon conversion reactions such as paraffin isomerization, olefin skeletal or double bond isomerization, disproportionation, alkylation, and transalkylation of aromatics are governed by constraints imposed by the channel size of the molecular sieve. Reactant selectivity occurs when a fraction of the feedstock is too large to enter the pores to react; while product selectivity occurs when some of the products can not leave the channels or do not subsequently react. Product distributions can also be altered by transition state selectivity in which certain reactions can not occur because the reaction transition state is too large to form within the pores. Selectivity can also result from configuration constraints on diffusion where the dimensions of the molecule approach that of the pore system. Non-selective reactions on the surface of the molecular sieve, such reactions on the surface acid sites of the molecular sieve, are generally not desirable as such reactions are not subject to the shape selective constraints imposed on those reactions occurring within the channels of the molecular sieve.

Zeolites are comprised of a lattice silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, gallium oxide, indium oxide, and mixtures thereof can replace the alumina portion. Accordingly, the terms "zeolite", "zeolites" and "zeolite material", as used herein, shall mean not only materials containing silicon and, optionally, aluminum atoms in the crystalline lattice structure thereof, but also materials which contain suitable replacement atoms for such silicon and aluminum, such as gallosilicates, silicoaluminophosphates (SAPO) and aluminophosphates (ALPO). The term "aluminosilicate zeolite", as used herein, shall mean zeolite materials consisting essentially of silicon and aluminum atoms in the crystalline lattice structure thereof.

Synthetic zeolites are conventionally prepared by the crystallization of zeolites from a supersaturated synthesis mixture. The resulting crystalline product is then dried and calcined to produce a zeolite powder. Although the zeolite powder has good adsorptive properties, its practical applications are severely limited because it is difficult to operate fixed beds with zeolite powder. Therefore, prior to using the powder in commercial processes, the zeolite crystals are usually bound.

Mechanical strength is conventionally conferred on the zeolite provider by forming a zeolite aggregate such as a pill, sphere, or extrudate. The extrudate can be formed by extruding the zeohte in the presence of a non-zeolitic binder and drying and calcining the resulting extrudate. The binder materials used are resistant to the temperatures and other conditions, e.g., mechanical attrition, which occur in various hydrocarbon conversion processes. It is generally necessary that the zeolite be resistant to mechanical attrition, that is, the formation of fines which are small particles, e.g., particles having a size of less than 20 microns. Examples of suitable binders include amorphous materials such as alumina, silica, titania, and various types of clays.

Although such bound zeolite aggregates have much better mechanical strength than the zeolite powder, when the bound zeolite is used in a catalytic conversion process, the performance of the catalyst, e.g., activity, selectivity, activity maintenance, or combinations thereof, can be reduced because of the binder. For instance, since the binder is typically present in amounts of up to about 60 wt. % of zeolite, the binder dilutes the adsorptive properties of the zeolite aggregate. In addition, since the bound zeolite is prepared by extruding or otherwise forming the zeolite with the binder and subsequently drying and calcining the extrudate, the amorphous binder can penetrate the pores of the zeolite or otherwise block access to the pores of the zeolite, or slow the rate of mass transfer to and from the pores of the zeolite which can reduce the effectiveness of the zeolite when used in hydrocarbon conversion processes and other applications. Furthermore, when a bound zeolite is used in catalytic conversions processes, the binder may affect the chemical reactions that are taking place within the zeolite and also may itself catalyze undesirable reactions which can result in the formation of undesirable products. Therefore, it is desirable that zeolite catalysts used in hydrocarbon conversion not include deleterious amounts of such binders.

In certain hydrocarbon conversion processes, it is sometimes desirable that the catalyst used in the process be tailored to maximize its performance. For instance, it is sometimes desirable that the catalyst used in a hydrocarbon conversion process be a multifunctional catalyst, e.g., a bifunctional catalyst having the capability of performing two or more functions. A bifunctional catalyst comprises two separate catalysts which induce separate reactions. The reaction products can be separate or the two catalysts can be used together such that the reaction product of one catalyst is transported to and reacts on a catalyst site of the second catalyst. Also, since one of the benefits of using a zeolite catalyst is that the catalyst is shape selective and non-selective reactions on the surface of the zeolite are usually not desirable, it is sometimes desirable that the catalyst used in a hydrocarbon conversion process have the capability of preventing or at least reducing unwanted reactions which may take place on the surface of the zeolite catalyst by selectively sieving molecules in the feedstream based on their size or shape to prevent undesirable molecules present in the feedstream from entering the catalytic phase of the zeolite catalyst and reacting with the catalyst. In addition, the performance of a zeolite catalyst can sometimes be maximized if the catalyst selectively sieves desired molecules based on their size or shape in order to prevent the molecules from exiting the catalyst phase of the catalyst.

The present invention provides a zeolite bound zeolite catalyst for use in hydrocarbon conversion processes which does not contain substantial amounts of a non-zeolitic binder and comprises core and binder zeolites that can be tailored to optimize its performance.

SUMMARY OF THE INVENTION

The present invention is directed to a zeolite bound zeolite catalyst which comprises first crystals of a first zeolite and a binder comprising second crystals of a second zeolite and the use of the zeolite bound zeolite catalyst in hydrocarbon conversion processes. The structure type of the second zeolite is different from the structure type of the first zeolite. The structure type of the first and second zeolites and their composition, e.g. catalytic activity, are preferably tailored to provide a zeolite bound zeolite catalyst having enhanced performance. For example, the zeolite bound zeolite catalyst can be tailored to be multifunctional and/or can be tailored to prevent undesirable molecules from entering or exiting the catalytic phase of the zeolite bound zeolite catalyst.

The zeolite bound zeolite catalyst of the present invention has application in hydrocarbon conversion processes and finds particular application in acid catalyzed reactions such as catalytic cracking, alkylation, dealkylation, disproportionation, and transalkylation reactions. In addition, the zeolite bound zeolite catalyst system of the present invention has particular application in other hydrocarbon conversion processes where cracking is not desired which include catalyzed reactions, such as, dehydrogenation, hydrocracking, isomerization, dewaxing, oligomerization, and reforming.

DETAILED DESCRIPTION OF THE INVENTION

The present invention is directed to a zeolite bound zeolite catalyst and a process for converting organic compounds by contacting the organic compounds under conversion conditions with the zeolite bound zeolite catalyst. The zeolite bound zeolite catalyst comprises first crystals of a first zeolite and a binder comprising second crystals of a second zeolite. The structure type of the second zeolite is different from the structure type of the first zeolite. The use of the second crystals of a second zeolite as a binder results in a catalyst which provides a means for controlling undesirable reactions taking place on or near the external surface of the first zeolite crystals and/or affects the mass transfer of hydrocarbon molecules to and from the pores of the first zeolite. Alternatively, the second zeolite binding crystals, if desired, can have catalytic activity, can function as a catalyst carrier, and/or can selectively prevent undesirable molecules from entering or exiting the pores of the first zeolite.

Unlike typical zeolite catalysts used in hydrocarbon conversion processes which are normally bound with silica or alumina or other commonly used amorphous binders to enhance the mechanical strength of the zeolite, the zeolite catalyst of the present invention generally does not contain significant amounts of non-zeolitic binders. Preferably, the zeolite bound zeolite catalyst contains less than 10 percent by weight, based on the weight of the first and second zeolite, of non-zeolitic binder, more preferably contains less than 5 percent by weight, and, most preferably, the catalyst is substantially free of non-zeolitic binder. Preferably, the second zeolite crystals bind the first zeolite crystals by adhering to the surface of the first zeolite crystals thereby forming a matrix or bridge structure which also holds the first crystals particles together. More preferably, the second zeolite particles bind the first zeolite by intergrowing so as to form a coating or partial coating on the larger first zeolite crystals and, most preferably, the second zeolite crystals bind the first zeolite crystals by intergrowing to form an attrition resistant over-growth over the first zeolite crystals.

Although the invention is not intended to be limited to any theory of operation, it is believed that one of the advantages of the zeolite bound zeolite catalyst of the present invention is obtained by the second zeolite crystals controlling the accessibility of the acid sites on the external surfaces of the first zeolite to reactants. Since the acid sites existing on the external surface of a zeolite catalyst are not shape selective, these acid sites can adversely affect reactants entering the pores of the zeolite and products exiting the pores of the zeolite. In line with this belief, since the acidity and structure type of the second zeolite can be carefully selected, the second zeolite does not significantly adversely affect the reactants exiting the pores of the first zeolite which can occur with conventionally bound zeolite catalysts and may beneficially affect the reactants exiting the pores of the first zeolite. Still further, since the second zeolite is not amorphous but, instead, is a molecular sieve, hydrocarbons may have increased access to the pores of the first zeolite during hydrocarbon conversion processes. Regardless of the theories proposed, the zeolite bound zeolite catalyst, when used in catalytic processes, has one or more of the improved properties which are disclosed herein.

The terms "acidity", "lower acidity" and "higher acidity" as applied to zeolite are known to persons skilled in the art. The acidic properties of zeolite are well known. However, with respect to the present invention, a distinction must be made between acid strength and acid site density. Acid sites of a zeolite can be a Bronsted acid or a Lewis acid. The density of the acid sites and the number of acid sites are important in determining the acidity of the zeolite. Factors directly influencing the acid strength are (i) the chemical composition of the zeolite framework, i.e., relative concentration and type of tetrahedral atoms, (ii) the concentration of the extra-framework cations and the resulting extra-framework species, (iii) the local structure of the zeolite, e.g., the pore size and the location, within the crystal or at/near the surface of the zeolite, and (iv) the pretreatment conditions and presence of co-adsorbed molecules. The amount of acidity is related to the degree of isomorphous substitution provided, however, such acidity is limited to the loss of acid sites for a pure $SiO_2$ composition. As used herein, the terms "acidity", "lower acidity" and "higher acidity" refers to the concentration of acid sites irregardless of the strength of such acid sites which can be measured by ammonia absorption.

First and second zeolites suitable for use in the zeolite bound zeolite catalyst of the present invention include large pore size zeolites, intermediate pore size zeolites, and small pore size zeolites. These zeolites are described in "Atlas of Zeolite Structure Types", eds. W. H. Meier and D. H. Olson, Butterworth-Heineman, Third Edition, 1992, which is hereby incorporated by reference. A large pore zeolite generally has a pore size greater than about 7 Å and includes for example LTL, VFI, MAZ, MEI, FAU, EMT, OFF, BEA, and MOR structure type zeolites (IUPAC Commission of Zeolite Nomenclature). Examples of large pore zeolites, include, for example, mazzite, mordenite, offretite, zeolite L, VPI-5, zeolite Y, zeolite X, omega, Beta, ZSM-3, ZSM-4, ZSM-18, and ZSM-20. An intermediate pore size zeolite generally has a pore size from about 5 Å, to about 7 Å and includes for example, MFI, MFS, MEL, MTW, EUO, MTT, HEU, FER, and TON structure type zeolites (IUPAC Commission of Zeolite Nomenclature). Examples of intermediate pore size zeolites, include ZSM-5, ZSM-12, ZSM-22, ZSM-23, ZSM-34, ZSM-35, ZSM-38, ZSM-48, ZSM-50, silicalite, and silicalite 2. A small pore size zeolite generally has a pore size from about 3 Å to about 5.0 Å and includes for example, CHA, ERI, KFI, LEV, and LTA structure type zeolites (IUPAC Commission of Zeolite Nomenclature). Examples of small pore zeolites include ZK-4, ZK-14, ZK-21, ZK-22, ZK-5, ZK-20, zeolite A, erionite, chabazite, zeolite T, gemlinite, and clinoptilolite.

Preferred first and second zeolites used in the zeolite bound zeolite catalyst comprise compositions which have the following molar relationship:

$$X_2O_3:(n)YO_2,$$

wherein X is a trivalent element, such as titanium, boron, aluminum, iron, and/or gallium, Y is a tetravalent element such as silicon, tin, and/or germanium, and n has a value of at least 2, said value being dependent upon the particular type of zeolite and the trivalent element present in the zeolite.

When either zeolite has intermediate pore size, the zeolite preferably comprises a composition having the following molar relationship:

$$X_2O_3:(n)YO_2,$$

wherein X is a trivalent element, such as aluminum, and/or gallium, Y is a tetravalent element such as silicon, tin, and/or germanium; and n has a value greater than 10, said value being dependent upon the particular type of zeolite and the trivalent element present in the zeolite. When the first or second zeolite has a MFI structure, n is preferably greater than 20.

As known to persons skilled in the art, the acidity of a zeolite can be reduced using many techniques such as by dealumination and steaming. In addition, the acidity of a zeolite is dependent upon the form of the zeolite with the hydrogen form having the highest acidity and other forms of the zeolite such as the sodium form having less acidity than the acid form. Accordingly, the mole ratios of silica to alumina and silica to gallia disclosed herein shall include not only zeolites having the disclosed mole ratios, but shall also include zeolites not having the disclosed mole ratios but having equivalent catalytic activity.

When the first zeolite is a gallium silicate intermediate pore size zeolite, the zeolite preferably comprises a composition having the following molar relationship:

$$Ga_2O_3:ySiO_2$$

wherein y is between about 24 and about 500. The zeolite framework may contain only gallium and silicon atoms or may also contain a combination of gallium, aluminum, and silicon. When the first zeolite is a MFI structure type gallium silicate zeolite, the second zeolite will preferably be an intermediate pore size zeolite having a silica to gallia mole ratio greater than 100. The second zeolite can also have higher silica to gallia mole ratios, e.g., greater than 200, 500, 1000, etc.

When the first zeolite used in the zeolite bound zeolite catalyst is an aluminosilicate zeolite, the silica to alumina mole ratio will usually depend upon the structure type of the first zeolite and the particular hydrocarbon process in which the catalyst system is utilized and is therefore not limited to any particular ratio. Generally, however, and depending on the structure type of the zeolite, the first zeolite will have a silica to alumina mole ratio of at least 2:1 and in some instances from 4:1 to about 7:1. For a number of zeolites, especially intermediate pore size zeolites, the silica to alumina mole ratio will be in the range of from about 10:1 to about 1,000:1. When the catalyst is utilized in acid catalyzed reactions such as cracking, the manufacture of paraxylene and benzene by the disproportionation of toluene, the alkylation of benzene or the like, the zeolite will be acidic and will preferably, when it is an intermediate pore size zeolite, have higher silica to alumina mole ratios, e.g., 20:1 to about 200:1. If the catalyst system is utilized in a process where acid catalyzed reactions may not desired, such as a the reforming of naphtha, the second zeolite will preferably exhibit reduced acid activity.

The structure type of the first zeolite will depend on the particular hydrocarbon process in which the zeolite catalyst system is utilized. For instance, if the catalyst system is used for the reforming of naphtha to aromatics, the zeolite type will preferably be LTL (example Zeolite L) and have a silica to alumina ratio from 4:1 to about 7:1. If the catalyst system is be used for xylene isomerization or the manufacture of paraxylene and benzene by the disproportionation of toluene, the first zeolite will preferably be an intermediate pore size zeolite, such as a MFI structure type (example ZSM-5). If the zeolite catalyst system is to be used for cracking paraffins, the preferred pore size and structure type will depend on the size of the molecules to be cracked and the desired product. The selection of the structure type for hydrocarbon conversion processes is known to persons skilled in the art.

The term "average particle size" as used herein, means the arithmetic average of the diameter distribution of the crystals on a volume basis. The average particle size of the crystals of the first zeolite is preferably from about 0.1 to about 15 microns. In some applications, the average particle size will preferably be at least about 1 to about 6 microns. In other applications such as the cracking of hydrocarbons, the preferred average particle size will be from about 0.1 to about 3.0 microns.

The second zeolite will have a structure type that is different from the first zeolite. The structure type of the second zeolite will depend on the intended use of the zeolite bound zeolite catalyst. For instance, if the zeolite bound zeolite catalyst is utilized as an isomerization/ethylbenzene dealkylation catalyst, the first zeolite is preferably selected such that the dealkylation of the ethylbenzene will occur at the catalytic phase of the first zeolite, and xylene isomerization would primarily occur at the catalytic phase of the second zeolite. If the catalyst is to be utilized in a cracking process, the second zeolite will preferably have acid activity and the structure type can be selected such that its pore size allows into its channels the larger molecules where they are subject to cracking into small products. After the larger molecules are cracked by the second zeolite, the cracked molecules can then enter the smaller pores of a first zeolite where they can be subject to further cracking, isomerization, or oligimerization depending on the desired resulting product. Alternatively, the pore size of the second zeolite can be smaller than the pore size of the first zeolite. In this embodiment, the large molecules enter the pores of the first zeolite where they are subject to cracking and then the cracked molecules enter the pores of the second zeolite where they can be subject to further conversion. The catalyst can also be tailored so that the second zeolite crystals sieve feed components entering the pores of the first zeolite or sieve product components exiting the channels of the first zeolite. For instance, if the zeolite bound zeolite catalyst of the present invention comprises an appropriate pore size second zeolite, it can function to sieve and sort out molecules based on their size or shape and thereby prevent undesirable molecules from entering or exiting, as the case may be, the catalytic phase of the first zeolite.

When the second zeolite is aluminosilicate zeolite, the silica to alumina mole ratio of the second zeolite, will usually depend upon the structure type of the second zeolite and particular hydrocarbon process in which the catalyst is utilized and is therefore not limited to any particular ratio. Generally, however, and depending on the structure type of the zeolite, the silica to alumina ratio will be at least 2:1. In applications where the aluminosilicate zeolite is an intermediate pore size zeolite and low acidity is desired, the second zeolite preferably has a silica to alumina mole ratio greater than the silica to alumina mole ratio of the first zeolite, and more preferably is greater than 200:1. The second zeolite can also have higher silica to alumina mole ratios, e.g., 300:1, 500:1, 1,000:1, etc. In certain applications, the second zeolite can be a Silicalite i.e., the second zeolite is a MFI structure type substantially free of alumina or Silicalite 2, i.e., the second zeolite is a MEL structure type substantially free of alumina. The pore size of the second zeolite will preferably be a pore size that does not adversely restrict access of the desired molecules of the hydrocarbon feedstream to the catalytic phase of the first zeolite. For instance, when the materials of the feedstream which are to be converted by the first zeolite have a size from 5 Å to 6.8 Å, the second zeolite will preferably be a large pore zeolite or an intermediate pore size zeolite.

The second zeolite is usually present in the zeolite bound zeolite catalyst in an amount in the range of from about 10 to about 60% by weight based on the weight of the first zeolite but the amount of second zeolite present will usually depend on the hydrocarbon process in which the catalyst is utilized. More preferably the amount of second zeolite present is from about 20 to about 50% by weight.

The second zeolite crystals preferably have a smaller size than the first zeolite crystals. The second zeolite crystals preferably have an average particle size of less than 1 micron, preferably from about 0.1 to less than 0.5 micron. The second zeolite crystals, in addition to binding the first zeolite particles and maximizing the performance of the catalyst will preferably intergrow and to form an overgrowth which coats or partially coats the first zeolite. Preferably, the coating will be resistant to attrition.

The zeolite bound zeolite catalyst is preferably prepared by a three step procedure. The first step involves the synthesis of the first zeolite core crystals. Processes for preparing the first zeolite are known to persons skilled in the art. For example, with respect to the preparation of a MFI structure type, such as ZSM-5, a preferred process comprises preparing a solution containing tetrapropyl ammonium hydroxide or bromide, alkali metal oxide, an oxide of aluminum, an oxide of silicon and water, heating the reaction mixture to a temperature of 80° C. to 200° C. for a period of from about four hours to eight days. The resulting gel forms solid crystal particles which are separated from the reaction medium, washed with water and dried. The resulting product can be calcined in air at temperatures of 400–550° C. for a period of 10–40 hours to remove tetrapropylammonium (TPA) cations.

Next, a silica-bound zeolite is prepared preferably by mixing a mixture comprising the zeolite crystals, a silica gel or sol, water and optionally an extrusion aid until a homogeneous composition in the form of an extrudable paste develops. The silica binder used in preparing the silica bound zeolite aggregate is preferably a silica sol and can contain various amounts of trivalent metal oxides such as alumina. The amount of zeolite in the dried extrudate at this stage will preferably range from about 40 to 90% by weight, more preferably from about 50 to 80% by weight, with the balance being primarily silica, e.g. about 20 to 50% by weight silica.

The resulting paste is then molded, e.g. extruded, and cut into small strands, e.g., 2 mm diameter extrudates, which are dried at 100–150° C. for a period of 4–12 hours and then calcined in air at a temperature of from about 400° C. to 550° C. for a period of from about 1 to 10 hours.

Optionally, the silica-bound aggregate can be made into a very small particles which have application in fluid bed processes such as catalytic cracking. This preferably involves mixing the zeolite with a silica containing matrix solution so that an aqueous solution of zeolite and silica binder is formed which can be sprayed dried to result in small fluidizable silica-bound aggregate particles. Procedures for preparing such aggregate particles are known to persons skilled in the art. An example of such a procedure is described by Scherzer (Octane-Enhancing Zeolitic FCC Catalysts, Julius Scherzer, Marcel Dekker, Inc. New York, 1990). The fluidizable silica-bound aggregate particles, like the silica bound extrudates described above, would then undergo the final step described below to convert the silica binder to a second zeolite.

The final step in the three step catalyst preparation process is the conversion of the silica present in the silica-bound zeolite to a second zeolite having a structure type different from the first zeolite. The crystals of the second zeolite bind the first zeolite crystals together. The first zeolite crystals are thus held together without the use of a significant amount of non-zeolite binder.

To prepare the zeolite bound zeolite, the silica-bound aggregate is preferably first aged in an appropriate aqueous solution at elevated temperature. Next, the contents of the solution and the temperature at which the aggregate is aged are selected to convert the amorphous silica binder into the desired second zeolite. The newly-formed second zeolite is produced as crystals. The crystals may grow on and/or adhere to the first zeolite crystals, and may also be produced in the form of new intergrown crystals, which are generally much smaller than the initial crystals, e.g., of sub-micron size. These newly formed crystals may grow together and interconnect.

The nature of the zeolite formed in the secondary synthesis conversion of the silica to zeolite may vary as a function of the composition of the secondary synthesis solution and synthesis aging conditions. The secondary synthesis solution is preferably an aqueous ionic solution containing a source of hydroxy ions sufficient to convert the silica to the desired zeolite. It is important, however, that the aging solution be of a composition which will not cause the silica present in the bound zeolite extrudate to dissolve out of the extrudate.

The first and second zeolites may be further ion exchanged as is known in the art either to replace at least in part the original metals present in the zeolite with a different cation, e.g. a Group IB to VIII of the Periodic Table metal such as nickel, copper, zinc, calcium or rare earth metal, or to provide a more acidic form of the zeolite by exchange of alkali metal with intermediate ammonium, followed by calcination of the ammonium form to provide the acidic hydrogen form. The acidic form may be readily prepared by ion exchange using a suitable acidic reagent such as ammonium nitrate. The zeolite catalyst may then be calcined at a temperature of 400–550° C. for a period of 10–45 hours to remove ammonia and form the acidic hydrogen form. Ion exchange is preferably conducted after formation of the zeolite bound zeolite catalyst. Particularly preferred cations are those which render the material catalytically active, especially for certain hydrocarbon conversion reactions. These include hydrogen, rare earth metals, and metals of Groups IIA, IIIA, IVA, IB, IIB, IIIB, IVB, and VIII of the Periodic Table of the Elements. For some hydrocarbon conversion processes, the zeolite bound zeolite catalyst will contain a catalytically active metal such as at least one Group VIII metal, such as for example, platinum, palladium, rhodium, osmium, iridium, and ruthenium.

The zeolite catalyst systems of the present invention can be used in processing hydrocarbon feedstocks. Hydrocarbon feed-stocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbon feed is to undergo, the feed can contain metal or can be free of metals. Also, the feed can also have high or low nitrogen or sulfur impurities.

The conversion of hydrocarbon feeds can take place in any convenient mode, for example, in fluidized bed, moving bed, or fixed bed reactors depending on the types of process desired.

Since the zeolite bound zeolite catalyst of the present invention has controlled acidity, does not contain a conventional binder which can adversely affect the access and/or contact of reactants to and with the active sites of the catalyst and can also cause undesirable side reactions to occur, and if desired, can be tailored to maximize its performance, the zeolite bound zeolite catalyst of the present invention by itself or in combination with one or more catalytically active substances can be used as a catalyst or support for a variety of organic, e.g., hydrocarbon compound, conversion processes. Examples of such conversion processes include, as non-limiting examples, the following:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (volume of the catalyst feed rate) from about 10 milliseconds to about 10 seconds.

(B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100 $hr^{-1}$.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 100 $hr^{-1}$ and an aromatic hydrocarbon/polyalkylaromatic hydrocarbon mole ratio of from about 1/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 100 $hr^{-1}$ and an aromatic hydrocarbon/alkylating agent mole ratio of from about 1/1 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1. The resulting product from the reaction are long chain alkyl aromatics which when subsequently sulfonated have particular application as synthetic detergents;

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$;

(I) The hydrocracking of heavy petroleum feedstocks, cyclic stocks, and other hydrocrack charge stocks. The zeolite catalyst system will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 to about 800 psig, a WHSV-olefin from about 0.4 hr$^{-1}$ to about 0.8 hr$^{-1}$, a WHSV-reformate of from about 1 hr$^{-1}$ to about 2 hr$^{-1}$ and, optionally, a gas recycle from about 1.5 to 2.5 vol/vol fuel gas feed.

(K) The alkylation of aromatic hydrocarbons, e.g., benzene, toluene, xylene, and naphthalene, with long chain olefins, e.g., $C_{14}$ olefin, to produce alkylated aromatic lube base stocks. Typical reaction conditions include temperatures from about 100° C. to about 400° C. and pressures from about 50 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 hr$^{-1}$ to about 10 hr$^{-1}$.

(M) The conversion of light paraffins to olefins and/or aromatics. Typical reaction conditions include temperatures from about 425° C. to about 760° C. and pressures from about 10 to about 2000 psig.

(N) The conversion of light olefins to gasoline, distillate and lube range hydrocarbons. Typical reaction conditions include temperatures of from about 175° C. to about 375° C. and a pressure of from about 100 to about 2000 psig.

(O) Two-stage hydrocracking for upgrading hydrocarbon streams having initial boiling points above about 200° C. to premium distillate and gasoline boiling range products or as feed to further fuels or chemicals processing steps. The first stage would be the zeolite catalyst system comprising one or more catalytically active substances, e.g., a Group VIII metal, and the effluent from the first stage would be reacted in a second stage using a second zeolite, e.g., zeolite Beta, comprising one or more catalytically active substances, e.g., a Group VIII metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10;

(P) A combination hydrocracking/dewaxing process in the presence of the zeolite bound zeolite catalyst comprising a hydrogenation component and a zeolite such as zeolite Beta. Typical reaction conditions include temperatures from about 350° C. to about 400° C., pressures from about 1400 to about 1500 psig, LHSVs from about 0.4 to about 0.6 and a hydrogen circulation from about 3000 to about 5000 SCF/bbl.

(Q) The reaction of alcohols with olefins to provide mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-zeolite) from about 0.1 hr$^{-1}$ to about 200 hr$^{-1}$ and an alcohol to olefin molar feed ratio from about 0.1/1 to about 5/1.

(R) The disproportionation of aromatics, e.g. the disproportionation toluene to make benzene and paraxylene. Typical reaction conditions include a temperature of from about 200° C. to about 760° C., a pressure of from about atmospheric to about 60 atmosphere (bar), and a WHSV of from about 0.1 hr$^{-1}$ to about 30 hr$^{-1}$.

(S) The conversion of naphtha (e.g. $C_6$–$C_{10}$) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the zeolite at a temperature in the range of from about 400° C. to 600° C., preferably 480° C. to 550° C. at pressures ranging from atmospheric to 40 bar, and liquid hourly space velocities (LHSV) ranging from 0.1 to 15.

(T) The adsorption of alkyl aromatic compounds for the purpose of separating various isomers of the compounds.

(U) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100.

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a zeolite bound zeolite at a temperature in the range of from about 250° C. to about 800° C., a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the zeolite bound zeolite catalyst. Thus, when the olefin feedstock contacts the catalyst in the liquid phase, temperatures of from about 10° C. to about 250° C. may be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, the, catalytic conversion conditions over the zeolite bound zeolite catalyst include a temperature of from about 100° C. to about 760° C., a pressure of from about 0.1 atmosphere (bar) to about 200 atmospheres (bar), a weight hourly space velocity of from about 0.08 hr$^{-1}$ to about 2,000 hr$^{-1}$.

Although many hydrocarbon conversion processes prefer that the second zeolite crystals have lower acidity to reduce undesirable reactions external to the first zeolite crystals, some processes prefer that the second zeolite crystals have higher acidity, e.g., cracking reactions.

Processes that find particular application using the zeolite bound zeolite catalyst of the present invention are those where two or more reactions are taking place within the zeolite bound zeolite catalyst. This catalyst would comprise two different zeolites that are each separately tailored to promote or inhibit different reactions. A process using such a catalyst benefits not only from greater apparent catalyst activity, greater zeolite accessibility, and reduced non-selective surface acidity possible with zeolite bound zeolites, but from a tailored catalyst system.

Examples of zeolite bound zeolite catalysts and exemplary uses are shown below in Table I:

TABLE I

| Zeolite Bound Zeolite Catalyst | First Zeolite | | Second Zeolite | | |
|---|---|---|---|---|---|
| | Structure Type | Zeolite | Structure Type | Zeolite | Use |
| A | MFI | ZSM-5 | MEL | Silicalite 2 | Disproportion of Toluene |
| B | OFF | Offretite | MAZ | Omega | Cracking |
| C | MAZ | Omega | MOR | Mordenite | Cracking |
| D | MEL | ZSM-11 | MFI | Silicalite | Disproportion of Toluene |
| E | MEI | ZSM-18 | MFI | ZSM-5 | Cracking |
| F | MFI | ZSM-5 | MTW | ZSM-12 | Cracking |
| G | MFI | ZSM-5 | TON | ZSM-22 | Oligomerization |
| H | MFS | ZSM-57 | TON | ZSM-22 | Oligomerization |
| I | VFI | VPI-5 | MTW | ZSM-12 | Oligomerization |
| J | BEA | Beta | FER | ZSM-35 | Cracking |
| K | FAU | Zeolite Y | MTT | ZSM-23 | Cracking |
| L | TON | ZSM-22 | MFI | Silicalite | Disproportion of Toluene |
| M | MFI | ZSM-5 | KFI | ZK-5 | Cracking |
| N | LTL | Zeolite L | FAU | Zeolite Y | Reforming |
| O | MFI | Silicalite | MEL | Silicalite 2 | Isomerization |
| P | MOR | Mordenite | MFI | Silicalite | Disproportionation of Toluene |
| Q | BEA | Beta | MFI | Silicalite | Disproportionation of Toluene |
| R | BEA | Beta | MEL | Silicalite 2 | Disproportionation of Toluene |
| S | MFI | Ga-MFI | MEL | Silicalite 2 | $C_2$–$C_5$ Aromatization |
| T | MEL | Ga-MEL | MFI | Silicalite | $C_2$–$C_5$ Aromatization |
| U | MOR | Mordenite | MEL | Silicalite 2 | Disproportionation of Toluene |

Examples of preferred zeolite bound zeolite catalyst systems include the following:

1. A zeolite bound zeolite catalyst system comprising an acidic second zeolite having cracking activity and an acidic first zeolite having acidic activity which is less than the acidic activity of the second zeolite and a smaller pore size than the second zeolite. The zeolite bound zeolite catalyst system finds particular application in cracking larger size molecules and isomerizing the smaller cracked molecules. Examples of suitable second zeolites include Beta, Mordenite and the like. Examples of suitable first zeolites are ZSM-5, ZK-5, ZSM-11 and the like.

2. A zeolite bound zeolite catalyst system comprising an acidic first zeolite having a large or medium pore zeolite with cracking activity and an acidic second zeolite having smaller pore size than the second zeolite and having cracking activity. An example of a suitable first zeolite ZSM-5 and an example of a suitable second zeolite is ZK-5. The zeolite bound zeolite catalyst system finds particular application in cracking larger size molecules and further cracking the smaller cracked molecules to produce ethylene.

3. A zeolite catalyst system comprising one zeolite (either the first or second zeolite) that has reduced acid activity and optionally contains a hydrogenation/dehydrogenation metal and another zeolite which has medium strength acidic activity and optionally a hydrogenation/dehydrogenation metal. The pore size of the zeolites will depend upon the type of process in which the catalyst system is utilized. For example, the catalyst system can be utilized in a combined xylene isomerization/ethylbenzene dealkylation process wherein the ethylbenzene is dealkylated to benzene and ethane and isomers of xylenes are isomerized to equilibrium amounts. In such a system, the first zeolite will preferably have a large or intermediate pore size zeolite and the second zeolite will also preferably have a larger or intermediate pore size zeolite.

4. A zeolite bound zeolite catalyst comprising a first acidic zeolite and a second zeolite which has little or no acidic activity. The pore size of the zeolites will depend on the type of process in which the catalyst is utilized. For example, if the catalyst is to be used in the manufacture of benzene and paraxylene by the disproportionation of toluene, the first zeolite will preferably have an intermediate pore size and the second zeolite can be selected to enhance performance of the first zeolite, e.g., to sieve undesired molecules either leaving the first zeolite phase or exiting the first zeolite phase, as the case may be or to control accessibility of the add sites on the external surfaces of its first zeolite to reactants. Catalysts A and D in Table I are examples of such a catalyst.

The zeolite-bound zeolite catalyst of the present invention has particular application in the vapor phase disproportionation of toluene. Such vapor phase disproportionation comprises contacting toluene under disproportionation conditions with the zeolite bound zeolite catalyst to yield a product mixture which comprises a mixture of unreacted (unconverted) toluene, benzene and xylene. In the more preferred embodiment, the catalyst is first selectivated prior to use in the disproportionation process to enhance conversion of toluene to xylene and to maximize the catalyst selectivity towards the production of paraxylene. Processes for selectivating the catalyst are known to persons skilled in the art. For instance, selectivation may be accomplished by exposing the catalyst in a reactor bed to a thermally decomposable organic compound, e.g. toluene, at a temperature in excess of the decomposition temperature of said compound, e.g. from about 480° C. to about 650° C., more preferably 540° C. to about 650° C., at a WHSV in the range of from about 0.1 to 20 lbs of feed per pound of catalyst per hour, at a pressure in the range of from about 1 to 100 atmospheres, and in the presence of 0 to about 2 moles of hydrogen, more preferably from about 0.1 to about 2 moles of hydrogen per mole of organic compound, and optionally in the presence of 0–10 moles of nitrogen or another inert gas per mole of organic compound. This process is conducted for a period of time until a sufficient quantity of coke has been deposited on the catalyst surface, generally at least about 2% by weight and more preferably from about 8 to about 40% by weight of coke. In a preferred embodiment, such a selectivation process is conducted in the presence of hydrogen in order to prevent rampant formation of coke on the catalyst.

Selectivation of the catalyst can also be accomplished by treating the catalyst with a selectivation agent such as an organosilicon compound. Examples of organosilicon compounds include polysiloxane including silicones, a siloxane, and a silane including disilanes and alkoxysilanes.

Silicone compounds that find particular application can be represented by the formula:

wherein $R_1$ is hydrogen, fluoride, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 2 to 1000. The molecular weight of the silicone compound employed is generally between 80 and 20,000 and preferably 150 to 10,000. Representative silicone compounds included dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, tetrachlorophenylmethyl silicone, tetrachlorophenylethyl silicone, tetrachlorophenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenylcyclotrisiloxane and octaphenylcyclotetrasiloxane. Mixtures of these compounds may also be used as well as silicones with other functional groups.

Useful siloxanes or polysiloxanes include as non-limiting examples hexamethylcyclotrisiloxane, octamethylcyclotetrasiloxane, decamethylcyclopentasiloxane, hexamethyldisiloxane, octamethytrisiloxane, decamethyltetrasiloxane, hexaethylcyclotrisiloxane, octaethylcyclotetrasiloxane, hexaphenylcyclotrisiloxane and octaphenylcyclotetrasiloxane.

Useful silanes, disilanes, or alkoxysilanes include organic substituted silanes having the general formula:

wherein R is a reactive group such as hydrogen, alkoxy, halogen, carboxy, amino, acetamide, trialkylsilyoxy $R_1$, $R_2$ and $R_3$ can be the same as R or can be an organic radical which may include alkyl of from 1 to 40 carbon atoms, alkyl or aryl carboxylic acid wherein the organic portion of the alkyl contains 1 to 30 carbon atoms and the aryl group contains 6 to 24 carbon which may be further substituted, alkylaryl and arylalkyl groups containing 7 to 30 carbon atoms. Preferably, the alkyl group for an alkyl silane is between 1 and 4 carbon atoms in chain length.

When used the vapor phase disproportionation of toluene, the catalyst can comprise a first phase of particles of MFI-type zeolite crystals having a micron average particle size from about 2 to about 6, a silica to alumina mole ratio of from about 20 to about 200:1, preferably, 25:1 to about 120:1, having adhered structurally to the surfaces thereof particles of a second MEL-type zeolite binder phase having an average particle size of less than about 0.1 micron and having a alumina to silica mole ratio in excess of about 200:1 to about 10,000:1 and most preferably greater than 500:1 including Silicalite 2.

Once the catalyst has been selectivated to the desired degree, reactor selectivation conditions are changed to disproportionation conditions. Disproportionation conditions include a temperature between about 400° C. and 550° C., more preferably between about 425° C. and 510° C., at a hydrogen to toluene mole ratio of from 0 to about 10, preferably between about 0.1 and 5 and more preferably from about 0.1 to 1, at a pressure between about 1 atmosphere and 100 atmospheres and utilizing WHSV of between about 0.5 and 50.

The disproportionation process may be conducted as a batch, semi-continuous or continuous operation using a fixed or moving bed catalyst system deposited in a reactor bed. The catalyst may be regenerated after coke deactivation by burning off the coke to a desired extent in an oxygen-containing atmosphere at elevated temperatures as know in the art.

The zeolite bound zeolite of the present invention also finds particular application as a catalyst in a process for isomerizing one or more xylene isomers in a $C_8$ aromatic feed to obtain ortho-, meta-, and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio.

Ethylbenzene in the feed is either removed from the stream or is converted during the process to xylenes or to benzene which are easily separated by distillation. The isomerate is blended with fresh feed and the combined stream is distilled to remove heavy and light by-products. The resultant $C_8$ aromatics stream is then recycled to repeat the cycle.

It is important that xylene isomerization catalysts produce a near equilibrium mixture of xylenes and it is also usually desirable that the catalyst convert ethylbenzene with very little net loss of xylenes. The zeolite bound zeolite catalyst finds particular application in this regard. The silica to alumina mole ratios of the first zeolite and second zeolite can be selected to balance xylene isomerization and ethylbenzene dealkylation while minimizing undesirable side reactions. Accordingly, the zeolite catalyst of the present invention finds particular application in a hydrocarbon conversion process which comprises contacting a $C_8$ aromatic stream containing one or more xylene isomers or ethylbenzene or a mixture thereof, under isomerization conditions with the zeolite bound zeolite catalyst. Preferably, at least 30% of the ethylbenzene is converted.

In the vapor phase, suitable isomerization conditions include a temperature in the range 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 3.0 to 30.0 moles of hydrogen per mole of alkylbenzene. If hydrogen is used, the metal components of the catalyst preferably include 0.1 to 2.0 wt. % of a hydrogenation/dehydrogenation component selected from Group VIII of the Periodic Table of Elements, especially platinum, palladium, or nickel. By Group VIII metal component, it is meant the metals and their compounds such as oxides and sulfides.

In the liquid phase, suitable isomerization conditions include a temperature in the range 150° C.–375° C., a pressure in the range 1–200 atm abs, and a WHSV in the range 0.5–50. Optionally, the isomerization feed may contain 10 to 90 wt. % of a diluent such as toluene, trimethylbenzenes, naphthenes, or paraffins.

The zeolite bound zeolite catalyst of the present invention are especially useful as a catalyst in a process for cracking a naphtha feed, e.g., $C_4^+$ naphtha feed, particularly a $C_4^-$ 290° C. naphtha feed to produce low molecular weight olefins, e.g., $C_2$ through $C_4$ olefins, particularly ethylene and propylene. Such a process is preferably carried out by contacting the naphtha feed at temperatures ranging from 500° C. to about 750° C., more preferably 550° C. to 675° C., at a pressure from subatmospheric up to 10 atmospheres, but preferably from about 1 atmosphere to about 3 atmospheres.

The zeolite bound zeolite catalyst of the present invention is especially useful as a catalyst in the transalkylation of polyalkylaromatic hydrocarbons. Examples of suitable polyalkylaromatic hydrocarbons include di-, tri-, and tetra-alkyl aromatic hydrocarbons, such as diethylbenzene, triethylbenzene, diethylmethylbenzene (diethyltoluene), diisopropyl-benzene, triisopropylbenzene, diisopropyltoluene, dibutylbenzene, and the like. Preferred polyalkylaromatic hydrocarbons are the dialkyl benzenes. Particularly preferred polyalkyl-aromatic hydrocarbons are diisopropylbenzene and diethylbenzene.

The transalkylation process will preferably have a molar ratio of aromatic hydrocarbon to polyalkylaromatic hydrocarbon of preferably from about 0.5:1 to about 50:1, and more preferably from about 2:1 to about 20:1. The reaction temperature will preferably range from about 340° C. to 500° C. to maintain at least a partial liquid phase, and the pressure will be preferably in the range of about 50 psig to 1,000 psig, preferably 300 psig to 600 psig. The weight hourly space velocity will range from about 0.1 to 10.

The zeolite bound zeolite catalyst is also useful in processes for converting aromatic compounds from paraffins. Example of suitable paraffins including aliphatic hydrocarbons containing 2 to 12 carbon atoms. The hydrocarbons may be straight chain, open or cyclic and may be saturated or unsaturated. Example of hydrocarbons include propane, propylene, n-butane, n-butenes, isobutane, isobutene, and straight- and branch-chain and cyclic pentanes, pentenes, hexanes, and hexenes.

The aromatization conditions include a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The zeolite bound zeolite catalyst used in the aromatization process preferably comprises first crystals of an intermediate pore size zeolite such a MFI type zeolite (example ZSM-5), and second crystals of a intermediate pore size such as a MEL structure type. The catalyst preferably contains gallium. Gallium may be incorporated into the during synthesis of the zeolite or it may be exchanged or impregnated or otherwise incorporated into the zeolite after synthesis. Preferably 0.05 to 10, and most preferably 0.1 to 2.0 wt. % gallium is associated with the zeolite bound zeolite catalyst. The gallium can be associated with the first zeolite, second zeolite, or both zeolites.

The following examples illustrate the invention.

EXAMPLE 1

Preparation of Zeolite KL Bound by Offeretite

Zeolite KL crystals were prepared from a synthesis gel having the following composition expressed in moles of pure oxide:

2.7 $K_2O$/1.0 $Al_2O_3$/9.2 $SiO_2$:150 $H_2O$

The gel was prepared as follows:

Aluminum hydroxide was dissolved in a aqueous solution of potassium hydroxide (50% pure KOH) to form Solution A. After dissolution, water loss was corrected. A separate solution, Solution B, was prepared by diluting colloidal silica (LUDOX HS 40) with water.

Solutions A and B were mixed and preheated to 150° C. and held at that temperature for 90 hours to bring about crystallization. After crystallization, the crystals were washed and calcined.

The formed zeolite KL was highly crystalline and the crystals were cylindrical and had a length from 0.5 to 1.5 microns and a diameter from 0.5 to 2.0 microns.

The zeolite KL was formed into silica bound extrudates as follows:

| Components Used for Preparation | Quantity (Grams) |
| --- | --- |
| Zeolite KL Crystals | 650.00 |
| Water | 160.51 |
| Silica $H_2O$ Gel (Aerosil 200) | 61.06 |
| Silica Sol (Nalcoag 1034 A) | 640.55 |
| Methocel (Hydroxypropyl methyl cellulose extrusion Acid) | 3.54 |

The above components were mixed in a household mixed in the order shown. After adding the methocel, a thickened and extrudable dough was obtained. The total mixing time was about 28 minutes.

The dough was extruded into 2 mm extrudates, dried overnight at 100° C., broken into 0.5–1 mm pieces and then calcined at 505° C. for 6 hours in air.

Composition of silica-bound extrudates:

Zeolite YL: 70 wt. %

$SiO_2$ Binder: 30 wt. %

The silica-bound zeolite KL extrudates were converted into zeolite KL bound by offretite as follows:

| Components Used for Preparation | Quantity (grams) |
| --- | --- |
| Solution A | |
| KOH pellets | 7.1124 |
| Aluminum Hydroxide | 4.9792 |
| Water | 35.02 |
| Solution B | |
| Tetramethyl ammoniumchloride | 4.1121 |
| $H_2O$ | 34.170 |

Solution A was prepared by dissolving the ingredients into boiling water and cooling the solution to ambient temperature. Water loss due to boiling was corrected.

Solution A was poured into a 300 ml stainless steel autoclave. Solution B was poured into the contents of the autoclave. The two solutions were mixed by swirling the autoclave. Finally, 50.02 grams of the silica-bound zeolite KL extrudates were added into the contents of the autoclave. The molar composition of synthesis mixture was:

2.20 K$_2$O/1.50 TMAC/1.26 Al$_2$O$_3$/10 SiO$_2$/160 H$_2$O

In the mixture, the silica is present as the binder in the extrudate.

The autoclave was heated up to 150° C. in 2 hours and kept at this temperature for 72 hours. After the aging period, the autoclave was opened and the product-extrudates were collected.

The product was washed in a Buechner funnel to a pH of 9.6. The product was dried overnight at 150° C. and subsequently calcined in air for 16 hours at 500° C. The amount of product was 55.6 grams and consisted of zeolite KL crystals which were bound by an overgrowth of offretite crystals The product had excellent strength.

The product extrudates were characterized by x-ray diffraction (XRD), scanning electron microscopy (SEM) and hexane adsorption, with the following results:

| XRD: | Showed the presence of zeolite L and offretite. The product had excellent crystallinity and no amorphous silica was present. |
|---|---|
| SEM: | Micrographs showed that the Zeolite KL crystals are overgrown with newly formed offretite crystals. |
| Hexane Adsorption: | 7.8 wt. % |

EXAMPLE 2

Preparation of Zeolite Y Bound by EMT Structure Type Zeolite

Zeolite Y crystals were formed into silica bound Zeolite Y as follows:

| Components Used for Preparation | Quantity (Grams) | Component No. |
|---|---|---|
| Zeolite Y Crystals | 200.00 | 1 |
| Water | 133.39 | 2 |
| SiO$_2$ gel (Ketjensil SM 604) | 20.93 | 3 |
| Silica sol (NALCOAG 1034 A) | 197.74 | 4 |
| Methocel | 1.12 | 5 |

Components 1 and 3 were mixed in the bowl of a household mixer. Next, components 2 and 4 were added to the bowl and the contents were mixed. Component 5 was then added to the bowl and the mixing continued. Total mixing time was about 28 minutes. A plastic extrudable dough was obtained. The dough was extruded into 2 mm extrudates. The extrudates were dried overnight at 150° C. and then calcined for 7.5 hours at 525° C. The extrudates contained 30.09 weight percent silica.

The silica bound zeolite Y extrudates were converted into Zeolite Y bound by EMT structure type zeolite as follows:

| Components used for Preparation | Quantity, (Grams) | Component No. |
|---|---|---|
| NaOH (98.6%) | 3.00 | 1 |
| Al(OH)$_3$ (98.5%) | 2.53 | 2 |
| Water | 8.64 | 3 |
| Rinse Water | 14.93 | 4 |
| Crown-ether 18-6 | 3.25 | 5 |
| Water | 18.17 | 6 |
| Water | 9.45 | 7 |
| Silica Bound Zeolite Y | 32.0 | 8 |

Components 1 and 2 were dissolved into component 3 by boiling to form a solution. In a 100 ml. plastic bottle, component 5 was dissolved into component 6. Component 7 was added to the contents of the plastic bottle. The solution was added together with component 4 into the plastic bottle. The bottle was mixed to ensure a homogeneous mixture. Finally component 8 was then added to the bottle. The molar composition of the synthesis mixture was:

2.32 Na$_2$O/0.77 C.E. 18-6/Al$_2$O$_3$/10 SiO$_2$/183 H$_2$O

The plastic bottle was placed into a 98° C. oil bath. After 15 days of heating at that temperature, crystallization was stopped. The product extrudates were washed 5 times with 800 ml water at 60° C. The conductivity of the last wash water was 70 µS/cm. The product was dried overnight at 120° C. Next, the extrudates were calcined at 500° C. for 9 hrs. The amount of product recovered after calcination was 31.70 gr.

Figure 1:
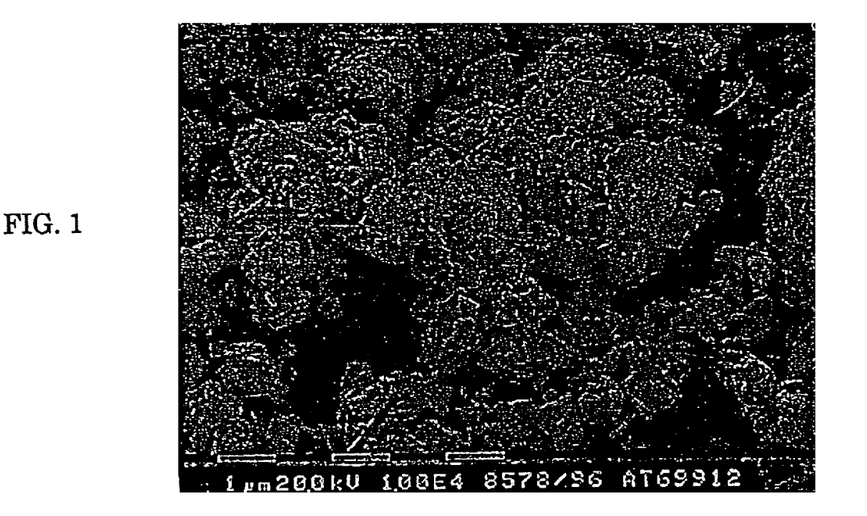
FIG. 1 shows SEM micrographs of the product of Example 2.

The product extrudates were characterized by x-ray diffraction (XRD), scanning electron microscopy (SEW) and hexane adsorption with the following results:

| XRD: | Showed excellent crystallinity and the presence of EMT structure type. No amorphous halo could be seen, which would have indicated the presence of unconverted silica. Zeolite P was completely absent. |
|---|---|
| SEM: | 10,000 times Micrographs (FIG. 1) show that the zeolite Y crystals are coated and glued with platelet like crystallites with newly formed EMT structure type zeolite. |
| Hexane adsorption: | 14.7 wt. % |

EXAMPLE 3

Preparation of MFI Bound by MEL

A MFI structure type zeolite having a silica to alumina mole ration of about 78 and bound by about 30% by weight silica was formed into a MFI structure type zeolite bound by Silicate 2 as follows:

| Components Use for Preparation | Quality (Grams) |
|---|---|
| Solution A | |
| NaOH pellets (98.6%) | 1.46 |
| Water | 33.35 |

| Components Use for Preparation | Quality (Grams) |
|---|---|
| Rinse Water | 16.48 |
| Solution B | |
| Tetragutylammonium bromide | 11.46 |
| Water | 33.93 |
| Rinse Water | 15.71 |

Solution A and B were poured into a 200 ml stainless steel autoclave. The contents of the autoclave were mixed. Finally, 75.02 grams of the silica bound MFI were added to the autoclave. The molar composition of the synthesis mixture was:

$0.48Na_2O/0.95\ TBA\ Br/10SiO_2/148H_2O$

The autoclave was placed into an oven at ambient temperature. The oven was heated to 150° C. and was maintained at 150° C. for 80 hours. The resulting product was washed 6 times at 60° C. with 2500 ml of water. The conductivity of the last wash water was 80 µS/cm. The product was dried overnight at 120° C. and calcined in air at 300° C. for 16 hours.

Figure 2:
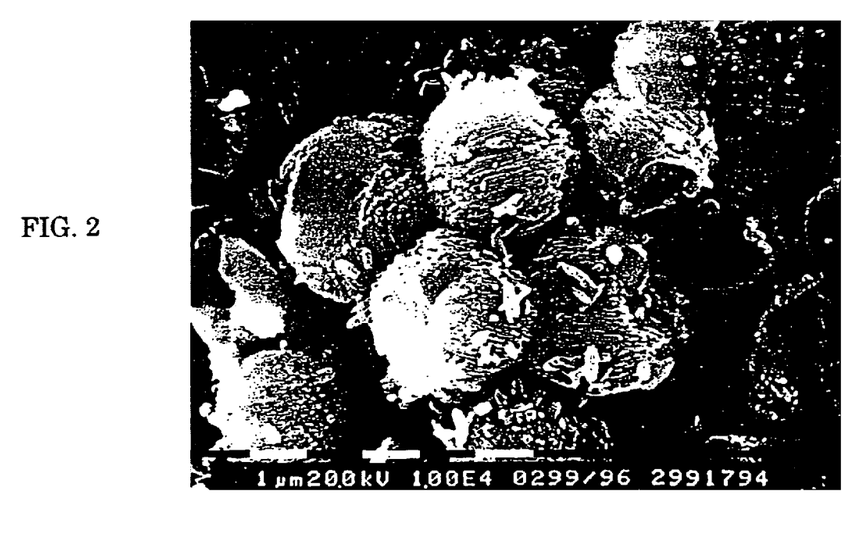
FIG. 2 shows SEM micrographs of the product of Example 3.

The product was analyzed by XRD and SEM with the following results:

| XRD: | Showed excellent crystallinity and the presence of MEL structure type zeolite. |
|---|---|
| SEM: | 10,000 times Micrographs (FIG. 2) show that the MFI crystals are intergrown with smaller crystals. |

EXAMPLE 4

The calcined, zeolite bound zeolite catalyst described in Example 3, was selectivated by feeding toluene across the catalyst under the conditions set forth in Table II below:

TABLE II

| Selectivation Conditions | | |
|---|---|---|
| Hours | | 121 |
| Temperature (° F.) | | 1100 |
| Pressure (Psig) | | 225 |
| WHSV (#Feed/#Cat/Hr) | | 1 |
| H₂:Feed Toluene Ratio (moles) | Initial | 0.21:1 |
| | Final | 0.35:1 |
| Hydrocarbon Partial Pressure | Initial | 64.6 Psia |
| | Final | 62.2 Psia |

Following selectivation, the catalyst was used for the disproportionation of toluene under the test conditions shown in Table III below. The catalyst was evaluated under 3 separate test conditions as shown in Table III. On-oil catalyst performance for the catalyst is also shown in Table III.

TABLE III

| On-Oil Conditions | | | |
|---|---|---|---|
| | Test 1 | Test 2 | Test 3 |
| Temperature (° F.) | 842 | 827 | 839 |
| Pressure (Psig) | 300 | 300 | 500 |
| WHSV (##Hr.) | 3.0 | 3.0 | 4.2 |
| H₂:Feed Toluene Ratio (moles) | 1.0 | 0.5 | 1.0 |
| Hydrocarbon Partial Pressure (Psig) | 144 | 198 | 236 |

| On-Oil Catalyst Performance | | | |
|---|---|---|---|
| | Test 1 | Test 2 | Test 3 |
| Toluene Conversion (wt. %) | 29.9 | 29.8 | 29.8 |
| Paraxylene Selectivity PX/[PX + MX + OX]X100 | 87.7 | 87.1 | 87.9 |
| Benzene Yield (wt. %) | 13.6 | 13.4 | 13.5 |
| Xylene Yield (wt. %) | 14.2 | 14.6 | 14.0 |
| C₅ − Yield (wt. %) | 0.8 | 0.6 | 1.1 |
| C₉ + Yield (wt. %) | 0.7 | 0.8 | 0.8 |

The results show the high catalyst activity and PX selectivity of the MEL-bound MFI catalyst.

EXAMPLE 5

I. Catalyst A—ALPO-5 bound SAPO-34

SAPO-34 bound by 30% by weight alumina was formed into AlPO-5 bound SAPO-34 as follows:

Amounts of 4.18 grams of 85% aqueous $H_3PO_4$, 10.78 grams of water, and 2.65 grams of tripropylamine (TPA) were added to a 300 ml Teflon lined autoclave in the order listed. The mixture was stirred to give a homogeneous solution. Next, 10 grams of dried extrudates (1/16" diameter) of the alumina bound SAPO-34 were added to the contents in the autoclave. The extrudates were completely covered by the liquid. The molar composition of the synthesis mixture was:

$TPA/Al_2O_3/P_2O_5/H_2O$ of 0.63/1.0/0.62/23.4

In the mixture, the alumina accounts for only the alumina binder of the extrudate and the $P_2O_5$ accounts for only 85% aqueous $H_3PO_4$. The autoclave was sealed and the mixture was heated in 2 hours to 200° C. and held without stirring for 24 hours at 200° C. The autoclave was cooled to room temperature and the mother liquor was decanted. The extrudates were washed with de-ionized water until the conductivity of the filtrate was less than 100 micro-Siemens. XRD analysis showed typical patterns for both SAPO-34 and ALPO-5.

II. Catalyst B—ALPO-11 bound SAPO-34

SAPO-34 bound by 25% by weight alumina was formed into ALPO-11 bound SAPO-34 as follows:

Amounts of 6.36 grams of 85% aqueous $H_3PO_4$, 18.02 grams of water, and 2.82 grams of dipropylamine (DPA) were added to a 100 ml teflon lined autoclave in the order listed. The mixture was stirred to give a homogeneous solution. Next, 15.00 grams of dried extrudates (1/16" diameter) of the alumina bound SAPO-34 were added to the contents in the autoclave. The extrudates were completely covered by the liquid. The molar composition of the synthesis mixture was:

DPA/Al$_2$O$_3$/P$_2$O$_5$/H$_2$O of 0.76/0.75/1.0/30.9

In the mixture, the Al$_2$O$_3$ accounts for only the alumina binder of the extrudate and the P$_2$O$_5$ accounts for only the 85% aqueous H$_3$PO$_4$. The autoclave was sealed and heated in 2 hours to 200° C. and held without stirring for 22 hours at 200° C. The autoclave was cooled to room temperature and the mother liquor was decanted. The extrudates were washed with de-ionized water until the conductivity of the filtrate was less than 100 micro-Siemens. XRD analysis showed typical patterns for both SAPO-34 and ALPO-11.

EXAMPLE 6

Catalyst A and Catalyst B were tested for use in the conversion of oxygenates to olefins. The tests were carried out using the following procedure: 5.0 cc (approximately 2.7 grams) of each catalyst was mixed with 15 cc quartz beads and loaded into a ¾" outer diameter 316 stainless steel tubular reactor which was heated by three-zone electric furnaces. The first zone acted as the preheating zone, vaporized the feed. The temperature of the center zone of the furnace was adjusted to 450° C. and the pressure was maintained at 1 atm. The reactor was purged first with nitrogen at 50 cc/min flow rate for 30 minutes. The feed had a 4:1 molar ratio of water to methanol and was pumped into the reactor at a rate calibrated to give a flow rate of about 0.7 hr$^{-1}$ WHSV. The effluent was analyzed at pre-determined intervals by an on-line gas chromatography fitted with both a thermal conductivity detector and a flame ionization detector. The results of these tests are shown below in Table IV:

TABLE IV

|  | Olefins Yield Converion (wt. %) | |
|---|---|---|
|  | Catalyst A | Catalyst B |
| Methane | 5.7 | 1.6 |
| Ethylene | 24 | 45 |
| Propylene | 41 | 38 |
| C$_4$ | 27 | 15 |

The data shows that the catalysts have good propylene selectivity and by tailoring the catalyst, product distribution can be varied.

EXAMPLE 7

A sample comprising 10 grams of the catalyst of Example 2 was loaded by ion exchange with a 0.6 wt percent palladium. The sample was exchanged using an aqueous mixture comprising 0.138 grams of Pd(NH$_3$)$_2$Cl$_2$ and 9.62 grams of NH$_4$NO$_3$ which was dissolved in 100 cc of demineralized water. The pH of the mixture was adjusted to greater than 7 using a NH$_4$OH solution (30 wt. % NH$_3$). This mixture, which contained the sample, was stirred for 24 hours at room temperature followed by two days without stirring at the same temperature. The Pd containing catalyst were then washed on a filter, oven dried at 90° C., and then calcined in air for 12 hours at 380° C.

Hydro-isomerization and hydro-cracking reactions were conducted. The tests were carried out by mixing two grams of the catalyst with 8 grams of quartz and then loading the catalyst into a 0.5 inch diameter stainless steel reactor. The total length of the reactor was 5 inches. The reactor was equipped with an axial thermo-well to measure the actual bed temperature. Reduction was carried out for 1 hour at 716° F., pressure (psig) of 58, and a hydrogen flow rate (cc/min) of 184. After reduction, a n-hexane feed was introduced into the hydrogen stream to give a n-hexane weight hourly space velocity (WHSV) of 0.95 hrs.$^{-1}$, a H$_2$/n-hexane molar ratio of 20 and a total pressure of 58 psig. Product samples were recovered on-line and analyzed by gas chromatography. The result of these tests are shown below in Table V.

TABLE V

|  | Run 1 | Run 2 | Run 3 |
|---|---|---|---|
| Temperature (F.) | 487 | 572 | 716 |
| n-hexane conversion (wt. %) | 44.5 | 81.1 | 95.8 |
| Yield branched hexanes (wt. %) (1) | 44.4 | 78.8 | 15.1 |
| Yield C$_1$ to C$_5$ paraffins (wt. %) | 0.1 | 2.0 | 79.4 |
| Hydro-isomerization Selectivity (wt. %) (2) | 99.7 | 97.2 | 15.7 |
| Hydro-cracking Selectivity (wt. %) (3) | 0.3 | 2.4 | 82.9 |

(1) wt. % sum of 2,2 di-methyl-butane; 2,3 di-methyl-butane; 2-methyl-pentane; 3-methyl-pentane
(2) (yield branched hexanes/n-hexane conversion) × 100
(3) (yield C$_1$ to C$_5$ paraffins/n-hexane conversion) × 100

The data shows that the catalyst has high activity and high hydroisomerization and hydrocracking selectivity.

What is claimed is:

1. A process for disproportionation of toluene comprising contacting a toluene feed stream under toluene disproportionation conditions with a zeolite bound zeolite catalyst which does not contain significant amounts of non-zeolitic binder, said catalyst comprising:

(a) first crystals of a first zeolite, and
    (b) a binder comprising second crystals of a second zeolite which has a structure type that is different from the structure type of said first zeolite; wherein said second crystals are intergrown to form an attrition resistant over-growth over said first crystals.

2. The process recited in claim 1, wherein said first crystals of said first zeolito have an average particle size greater than about 0.1 micron.

3. The process recited in claim 2, wherein said second crystals of said second zeolite have an average particle size that is less than said first crystals of said first zeolite.

4. The process of claim 2, wherein said toluene disproportionation is carried out at conditions comprising a temperature of from 100° C. to about 760° C. a pressure of 0.1 atmosphere to 100 atmospheres, a weight hourly space velocity of from about 0.08 hr$^{-1}$ to about 200 hr$^{-1}$.

5. The process recited in claim 4, wherein said first zeolite is a structure type selected from the group consisting of OFF, BEA, MAZ, MEI, FAU, EMT, LTL, VFI, MOR, MFI, MFS, MEL, MTW, MTT FER, EUO, HEU, TON, CHA, ERI, KFI, LEV, and LTA.

6. The process recited in claim 5, wherein said second zeolite is a structure type selected fibre the group consisting of OFF, BEA, MAZ, MEI, FAU, EMT, LTL, VFI, MOR, MFI, MFS, MEL, MTW, MTT, FER, EUO, HEU, TON, CHA, ERI, KFI, LEV, and LTA.

7. The process recited in claim 6, wherein said second zeolite has lower acidity than said first zeolite.

8. The process recited in claim 6, wherein said second zeolite has higher acidity than said first zeolite.

9. The process recited in claim 6, wherein the pore size of said first zeolite is larger than the pore size of said second zeolite.

10. The process recited in claim 6, wherein the pore size of said first zeolito is smaller than the pore size of said second zeolite.

11. The process recited in claim 6, wherein said first zeolite and said second zeolite are aluminosilicate zeolites or gallium silicate zeolites.

12. The process recited in claim 11, wherein said second zeolite is en aluminosilicate zeolite having a silica to alumina mole ratio greater than about 200:1.

13. The process recited in claim 12, wherein said first zeolite is an aluminosilicate zeolite having a silica to alumina mole ratio of from about 20:1 to about 200:1.

14. The process recited in claim 6, wherein said first zeolite and second zeolite are intermediate pore size zeolites.

15. The process recited in claim 6, wherein said catalyst contains less than 5% by weight of non-zeolitic binder based on weight of said first zeolite and said second zeolite.

* * * * *